United States Patent
Belzer et al.

(10) Patent No.: US 10,738,089 B2
(45) Date of Patent: Aug. 11, 2020

(54) USE OF A POLYPEPTIDE FOR EFFECTING IMMUNE SIGNALLING AND/OR AFFECTING INTESTINAL BARRIER FUNCTION AND/OR MODULATING METABOLIC STATUS

(71) Applicants: WAGENINGEN UNIVERSITEIT, Wageningen (NL); UNIVERSITE CATHOLIQUE DE LOUVAIN, Louvain-la-Neuve (BE)

(72) Inventors: Clara Belzer, Wageningen (NL); Willem Meindert De Vos, Ede (NL); Patrice Daniel Cani, Brussels (BE)

(73) Assignees: WAGENINGEN UNIVERSITEIT, Wageningen (NL); UNIVERSITÉ CATHOLIQUE DE LOUVAIN, Louvain-la-Neuve (BE)

( * ) Notice: Subject to any disclaimer, the term of this patent is extended or adjusted under 35 U.S.C. 154(b) by 0 days.

(21) Appl. No.: 15/571,175

(22) PCT Filed: May 4, 2016

(86) PCT No.: PCT/EP2016/060033
§ 371 (c)(1),
(2) Date: Nov. 1, 2017

(87) PCT Pub. No.: WO2016/177797
PCT Pub. Date: Nov. 10, 2016

(65) Prior Publication Data
US 2018/0265554 A1    Sep. 20, 2018

(30) Foreign Application Priority Data
May 6, 2015 (EP) .................................... 15166598

(51) Int. Cl.
| A61K 39/00 | (2006.01) |
| C07K 14/195 | (2006.01) |
| C12N 1/20 | (2006.01) |
| A61P 3/08 | (2006.01) |
| A61P 3/06 | (2006.01) |
| A61K 38/00 | (2006.01) |

(52) U.S. Cl.
CPC .............. *C07K 14/195* (2013.01); *A61P 3/06* (2018.01); *A61P 3/08* (2018.01); *C12N 1/20* (2013.01); *A61K 38/00* (2013.01)

(58) Field of Classification Search
CPC .................................................... C07K 14/195
See application file for complete search history.

(56) References Cited

U.S. PATENT DOCUMENTS

| 7,253,333 B2 * | 8/2007 | Tanaka ............... A01K 67/0339 800/10 |
| 9,173,910 B2 | 11/2015 | Kaplan et al. |
| 10,149,867 B2 | 12/2018 | Kaplan et al. |
| 10,149,870 B2 | 12/2018 | Kaplan et al. |
| 2006/0094649 A1* | 5/2006 | Keogh ............... C07K 14/4746 424/185.1 |
| 2012/0023095 A1 | 1/2012 | Wadycki et al. |
| 2012/0083514 A1 | 4/2012 | Prevost et al. |
| 2012/0183514 A1 | 7/2012 | Mercenier et al. |
| 2013/0224155 A1 | 8/2013 | Kaplan et al. |
| 2019/0046590 A1 | 2/2019 | Kaplan et al. |

FOREIGN PATENT DOCUMENTS

| EP | 2030623 | 3/2009 |
| WO | 01/058283 A1 | 8/2001 |
| WO | 2005/030133 A2 | 4/2005 |
| WO | 2006/101244 A2 | 9/2006 |
| WO | 2008028117 | 3/2008 |
| WO | WO 2008/076696 A2 | 6/2008 |
| WO | WO 2013/130773 A2 | 9/2013 |
| WO | WO 2014/075745 A1 | 5/2014 |
| WO | WO 2014/076246 A1 | 5/2014 |

OTHER PUBLICATIONS

Everard et al., "Cross-talk between Akkermansia muciniphila and intestinal epithelium controls diet-induced obesity" PNAS, May 28, 2013, vol. 110, No. 22, pp. 9066-9071.
Reunanen et al., "Akkermansia muciniphila Adheres to Enterocytes and Strengthens the Integrity of the Epithelial Cell Layer", Appl Environ Microbiol, Jun. 2015, vol. 81, No. 11, pp. 3655-3662.
Dorhout et al., "Oral administration of deuterium-labelled polyamines to sucking rat pups: Luminal uptake, metabolic fate and effects on gastrointestinal maturation", British Journal of Nutrition, Nov. 1997, pp. 639-654.
Lee et al., "Effect of Metformin on Metabolic Improvement and Gut Microbiota", Appl Environ Microbiol, Oct. 2014, vol. 80, No. 19, pp. 5935-5943.
Syngelaki et al., "Metformin versus Placebo in Obese Pregnant Women without Diabetes Mellitus", The New England Journal of Medicine, Feb. 4, 2016, 374(5), pp. 434-443.
Rajilic-Stojanovic et al., "The first 1000 cultured species of the human gastrointestinal microbiota", FEMS Microbiology Reviews, 2014, 38, pp. 996-1047.

(Continued)

*Primary Examiner* — Albert N Navarro
(74) *Attorney, Agent, or Firm* — Lathrop GPM LLP; James H. Velema, Esq.

(57) ABSTRACT

It has been found that an extracellular polypeptide derived from *Akkermansia municiphila* is capable of modulating and/or promoting gut mucosal immune system function and/or maintaining and/or restoring metabolic status and/or increasing the physical integrity of the gut mucosal barrier in a mammal. The polypeptide or host cells including such polypeptide may be employed to prevent and/or treat a variety of conditions that benefit from an increased physical integrity of the gut mucosal barrier and/or an improved gut mucosal immune system function and metabolic status.

26 Claims, 1 Drawing Sheet
Specification includes a Sequence Listing.

(56) References Cited

OTHER PUBLICATIONS

Derrien et al., "*Akkermansia muciniphila* gen. nov., sp. nov., a human intestinal mucin-degrading bacterium", International Journal of Systematic and Evolutionary Microbiology, 2004, 54, pp. 1469-1476.
Lukovac et al., "Differential Modulation by Akkermansia muciniphila and Faecalibacterium prausnitzii of Host Peripheral Lipid Metabolism and Histone Acetylation in Mouse Gut Organoids", mBio, Jul./Aug. 2014, vol. 5, No. 4, (10 pages).
Visweswaran et al., "Exploiting the peptidoglycan-binding motif, LysM, for medical and industrial applications", Appl Microbiol Biotechnol, 2014, 98, pp. 4331-4345.
Solanki et al., "Development of Microencapsulation Delivery System for Long-Term Preservation of Probiotics as Biotherapeutics Agent", BioMed Research International, 2013, vol. 2013, No. 620719, (21 pages).
Reunanen et al., "Characterization of the SpaCBA Pilus Fibers in the Probiotic Lactobacillus rhamnosus GG", Applied and Environmental Microbiology, Apr. 2012, vol. 78, No. 7, pp. 2337-2344.
Tailford et al., "Discovery of intramolecular trans-sialidases in human gut microbiota suggests novel mechanisms of mucosal adaptation", Nature Communications, 2015, 6:7624, (12 pages).
"Uncharacterized protein {EC0:00003131EMBL:ACD04926.1} Flags:Precursor" UNIPROT, Jul. 1, 2008, (1 page).
Van Passel et al., "The Genome of Akkermansia muciniphila, a Dedicated Intestinal Mucin Degrader, and Its Use in Exploring Intestinal Metagenomes", PLoS ONE, Mar. 2011, vol. 6, No. 3, (8 pages).
Everard et al., "Diabetes, obesity and gut microbiota", Best Practice & Research Clinical Gastroenterology, 2013, 27, pp. 73-83.
International Search Report, dated Jul. 25, 2016, from corresponding PCT Application PCT/EP2016/060033.
U.S. Appl. No. 14/443,829 2015/0306152, filed May 19, 2015 Oct. 19, 2015, Patrice Cani.
U.S. Appl. No. 15/759,381 2018/0250347, filed Mar. 12, 2018 Sep. 6, 2018, Patrice Cani.
U.S. Appl. No. 16/285,088 2019/0282630, filed May 7, 2019 Sep. 19, 2019, Patrice Cani.
U.S. Appl. No. 16/709,232, filed Dec. 10, 2019, Patrice Cani.
U.S. Appl. No. 16/709,238, filed Dec. 10, 2019, Patrice Cani.
U.S. Appl. No. 16/723,720, filed Dec. 20, 2019, Patrice Cani.
U.S. Appl. No. 16/723,723, filed Dec. 20, 2019, Patrice Cani.
Alhouayek et al., "Increasing endogenous 2-arachidonoylglycerol levels counteracts colitis and related systemic inflammation" FASEB J. 2011, 25(8):2711-2721.
Belzer et al., "Microbes inside-from diversity to function: the case of Akkermansia" ISME J. 2012, 6(8):1449-1458.
Ben-Shabat et al., "An entourage effect: inactive endogenous fatty acid glycerol esters enhance 2-arachidonoyl-glycerol cannabinoid activity" Eur J Pharmacol. 1998, 353(1):23-31.
Berer et al., Commensal microbiota and myelin autoantigen cooperate to trigger autoimmune demyelination, Nature. Oct. 26, 2011;479(7374):538-41.
De Weerth et al., "Crying in infants: on the possible role of intestinal microbiota in the development of colic", Gut Microbes. Sep.-Oct. 2013;4(5):416-21.
De Weerth et al., "Intestinal microbiota of infants with colic: development and specific signatures", Pediatrics. Feb. 2013;131(2):e550-8.
Delzenne et al., "Interaction between obesity and the gut microbiota: relevance in nutrition" Annu. Rev. Nutr. 2011.
Derrien et al., "Modulation of Mucosal Immune Response, Tolerance, and Proliferation in Mice Colonized by the Mucin-Degrader Akkermansia muciniphila" Frontiers in Microbiology 2011, 2:166, pp. 1-14.
Derrien et al., "The Mucin degrader Akkermansia muciniphila is an abundant resident of the human intestinal tract" Applied and Environmental Microbiology 2008, 74, 1646-1648.

Derrien et al., "*Akkermansia muciniphila* gen. nov., sp. nov., a human intestinal mucin-degrading bacterium" Int. J Sys. Evol. Microbiol. 2004, 54:1469-1476.
Everard et al., "Cross-talk between Akkermansia muciniphila and intestinal epithelium controls diet-induced obesity" NAS USA 2013, 110(22):9066-71.
Everard et al., "Responses of gut microbiota and glucose and lipid metabolism to prebiotics in genetic obese and liet-induced leptin-resistant mice" Diabetes, 2011, 60(11):2775-86.
Geurts et al., "Altered gut microbiota and endocannabinoid system tone in obese and diabetic leptin-resistant mice: impact on apelin regulation in adipose tissue" Frontiers in Microbiology 2011, 2:149.
Goris et al., "DNA-DNA hybridization values and their relationship to whole-genome sequence similarities", Int J Syst Evol Microbial. Jan. 2007;57(Pt 1):81-91.
Hansen et al., "2-0leoyl glycerol is a GPR119 agonist and signals GLP-1 release in humans" J Clin Endocrinol Metab. 2011, 96(9):E1409-17.
Hansen et al., "Early life treatment with vancomycin propagates Akkermansia muciniphila and reduces diabetes incidence in the NOD mouse" Diabetologia, 2012, 55(8):2285-2294.
Hsiao et al., "Microbiota modulate behavioral and physiological abnormalities associated with neurodevelopmental Disorders", Cell. Dec. 19, 2013;155(7):1451-63.
International Search Report and Written Opinion for PCT/EP2012/073972, dated Feb. 10, 2014, European Patent Office, Netherlands, 6 pages.
International Search Report and Written Opinion for PCT/EP2012/073011, dated Aug. 19, 2013, European Patent Office, Netherlands, 6 pages.
Johansson et al. "The two mucus layers of colon are organized by the MUC2 mucin, whereas the outer layer is a legislator of host-microbial interactions" PNAS U.S.A. 2011, 108 Suppl 1:4659-4665.
Le Roy et al., "Gut microbiota transplantation demonstrates its causal role in the development of type 2 diabetes and fatty liver" J Hepathol. 2012, 56:S21-S44.
Louis et al., The gut microbiota, bacterial metabolites and colorectal cancer, Nat Rev Microbial. Oct. 2014;12 ;10):661-72.
Muccioli et al., "The endocannabinoid system links gut microbiota to adipogenesis" Molecular Systems Biology 2010, 6:392.
Nylund et al., "Severity of atopic disease inversely correlates with intestinal microbiota diversity and butyrate-producing bacteria", Allergy. Feb. 2015;70(2):241-4.
Pott et al., "Innate immune signalling at the intestinal epithelium in homeostasis and disease" EMBO Rep. 2012, 13(8):684-698.
Rajilić-Stojanović et al., "Phylogenetic analysis of dysbiosis in ulcerative colitis during remission", Inflamm Bowel Dis. Mar. 2013;19(3):481-8.
Rajilić-Stojanović et al., "The first 1000 cultured species of the human gastrointestinal microbiota", FEMS Microbial Rev. 2014, 38(5): 996-1047.
Reunanen et al., "Akkermansia muciniphila Adheres to Enterocytes and Strengthens the Integrity of the Epithelial Sell Layer", Appl Environ Microbial. Jun. 2015;81(11):3655-62.
Scheperjans et al., "Gut microbiota are related to Parkinson's disease and clinical phenotype", Mov Disord. Mar. 2015;30(3):350-8.
Staley et al., "Classification of prokaryotic organisms: an overview", Krieg NR, Holt JG (eds) Bergey's Manual of Systemic Bacteriology, vol. 1. Baltimore, Williams and Wilkins. 1984: 1-4.
Tlaskalová-Hogenová et al., "The role of gut microbiota (commensal bacteria) and the mucosal barrier in the pathogenesis of inflammatory and autoimmune diseases and cancer: contribution of germ-free and gnotobiotic animal models of human diseases", Cellular & Molecular Immunology, 2011, 8:110-20.
Vaishnava et al., "The antibacterial lectin Reglllgamma promotes the spatial segregation of microbiota and host in the intestine" Science. 2011, 334(6053):255-258.
van Passel et al., "The genome of Akkermansia muciniphila, a dedicated intestinal mucin degrader, and its use in exploring intestinal metagenomes" PLoS One. 2011, 6(3):e16876.

(56) References Cited

OTHER PUBLICATIONS

Wlodarska et al., "An integrative view of microbiome-host interactions in inflammatory bowel diseases", Cell Host Microbe. May 13, 2015;17(5):577-91.
Zitvogel et al., "Cancer and the gut microbiota: an unexpected link", Sci Transl Med. Jan. 21, 2015;7(271):271ps1.
Zoetendal et al., "High-throughput diversity and functionality analysis of the gastrointestinal tract microbiota" Gut 2008, 57: 1605-1615.

* cited by examiner

SEQUENCE LISTING

<160> NUMBER OF SEQ ID NOS: 4

<210> SEQ ID NO 1
<211> LENGTH: 286
<212> TYPE: PRT
<213> ORGANISM: Akkermansia municiphila

<400> SEQUENCE: 1

```
Ile Val Asn Ser Lys Arg Ser Glu Leu Asp Lys Lys Ile Ser Ile Ala
1               5                   10                  15

Ala Lys Glu Ile Lys Ser Ala Asn Ala Ala Glu Ile Thr Pro Ser Arg
            20                  25                  30

Ser Ser Asn Glu Glu Leu Glu Lys Glu Leu Asn Arg Tyr Ala Lys Ala
        35                  40                  45

Val Gly Ser Leu Glu Thr Ala Tyr Lys Pro Phe Leu Ala Ser Ser Ala
    50                  55                  60

Leu Val Pro Thr Thr Pro Thr Ala Phe Gln Asn Glu Leu Lys Thr Phe
65                  70                  75                  80

Arg Asp Ser Leu Ile Ser Ser Cys Lys Lys Lys Asn Ile Leu Ile Thr
                85                  90                  95

Asp Thr Ser Ser Trp Leu Gly Phe Gln Val Tyr Ser Thr Gln Ala Pro
            100                 105                 110

Ser Val Gln Ala Ala Ser Thr Leu Gly Phe Glu Leu Lys Ala Ile Asn
        115                 120                 125

Ser Leu Val Asn Lys Leu Ala Glu Cys Gly Leu Ser Lys Phe Ile Lys
    130                 135                 140

Val Tyr Arg Pro Gln Leu Pro Ile Glu Thr Pro Ala Asn Asn Pro Glu
145                 150                 155                 160

Glu Ser Asp Glu Ala Asp Gln Ala Pro Trp Thr Pro Met Pro Leu Glu
                165                 170                 175

Ile Ala Phe Gln Gly Asp Arg Glu Ser Val Leu Lys Ala Met Asn Ala
            180                 185                 190

Ile Thr Gly Met Gln Asp Tyr Leu Phe Thr Val Asn Ser Ile Arg Ile
        195                 200                 205

Arg Asn Glu Arg Met Met Pro Pro Ile Ala Asn Pro Ala Ala Ala
    210                 215                 220

Lys Pro Ala Ala Ala Gln Pro Ala Thr Gly Ala Ala Ser Leu Thr Pro
225                 230                 235                 240

Ala Asp Glu Ala Ala Ala Pro Ala Ala Pro Ala Ile Gln Gln Val Ile
                245                 250                 255

Lys Pro Tyr Met Gly Lys Glu Gln Val Phe Val Gln Val Ser Leu Asn
            260                 265                 270

Leu Val His Phe Asn Gln Pro Lys Ala Gln Glu Pro Ser Glu
        275                 280                 285
```

<210> SEQ ID NO 2
<211> LENGTH: 864

```
<212> TYPE: DNA
<213> ORGANISM: Akkermansia municiphila

<400> SEQUENCE: 2
atcgtcaatt ccaaacgcag tgaactggac aaaaaaatca gcatcgccgc caaggaaatc      60
aagtccgcca atgctgcgga atcactccg agccgatcat ccaacgaaga gctggaaaaa      120
gaactgaacc gctatgccaa ggccgtgggc agcctggaaa cggcctacaa gcccttcctt     180
gcctcctccg cgctggtccc caccacgccc acggcattcc agaatgaact gaaaacattc     240
agggattccc tgatctcctc ctgcaagaaa agaacattc tcataacgga cacatcctcc      300
tggctcggtt tccaggttta cagcacccag gctccctctg ttcaggcggc ctccacgctg     360
ggttttgaat tgaaagccat caacagcctg gtcaacaaac tggcggaatg cggcctgtcc     420
aaattcatca aggtgtaccg ccccccagctc cccattgaaa cccggcgaa caatccggaa     480 gaatcggacg aagccgacca ggcccatgg actccatgc ctctggaaat agccttccag       540
ggcgaccggg aaagtgtatt gaaagccatg aacgccataa ccggcatgca ggactatctg     600
ttcacggtca actccatccg tatccgcaac gaacggatga tgccccctcc catcgccaat     660
ccggcagccg ccaaacctgc cgcggcccaa cccgccacgg gtgcggcttc cctgactccg     720
gcggatgagg cggctgcacc tgcagccccg gccatccagc aagtcatcaa gccttacatg     780
ggcaaggagc aggtctttgt ccaggtctcc ctgaatctgg tccacttcaa ccagcccaag     840
gctcaggaac cgtctgaaga ttaa                                           864

<210> SEQ ID NO 3
<211> LENGTH: 30
<212> TYPE: PRT
<213> ORGANISM: Akkermansia municiphila

<400> SEQUENCE: 3

Met Ser Asn Trp Ile Thr Asp Asn Lys Pro Ala Ala Met Val Ala Gly
1               5                   10                  15

Val Gly Leu Leu Leu Phe Leu Gly Leu Ser Ala Thr Gly Tyr
            20                  25                  30

<210> SEQ ID NO 4
<211> LENGTH: 90
<212> TYPE: DNA
<213> ORGANISM: Akkermansia municiphila

<400> SEQUENCE: 4
atgagcaatt ggattacaga caacaagccc gccgccatgg tcgcgggcgt gggacttctc      60
ttattcctgg ggttatccgc gacagggtac                                       90
```

USE OF A POLYPEPTIDE FOR EFFECTING IMMUNE SIGNALLING AND/OR AFFECTING INTESTINAL BARRIER FUNCTION AND/OR MODULATING METABOLIC STATUS

FIELD OF THE INVENTION

The invention relates to the fields of gut mucosal immune system, gut mucosal barrier, pharmaceutical, food or feed compositions comprising polypeptides and/or host cells, which are capable of modulating and/or promoting gut mucosal immune system function and/or maintaining and/or restoring and/or increasing the physical integrity of the gut mucosal barrier, and/or of maintaining, restoring or improving glucose and/or cholesterol and/or triglyceride homeostasis in a mammal (e.g. human). More specifically, the present invention provides compositions comprising Amuc-1100 polypeptide, or variants thereof. It has been found that Amuc-1100 is capable of interacting with the toll-like receptor 2 (TLR2) and/or modulating TLR2 and/or the NFk-B-dependent signalling pathway, and/or promoting cytokine release (e.g. IL-6, IL-8, and IL-10) from immune cells located in the vicinity of the mucosal gut barrier of a mammal (e.g. human), and/or is capable of maintaining, restoring or increasing the physical integrity of the gut mucosal barrier and/or of maintaining, restoring or improving glucose and/or cholesterol and/or triglyceride homeostasis in a mammal and/or is capable of improving the metabolic or immune status of a mammal. The Amuc-1100 polypeptide may be used to prevent or treat a variety of diseases or conditions as set forth herein.

BACKGROUND OF THE INVENTION

Increased permeability or hyperpermeability of the gut mucosal barrier is thought to play a role in several disorders and conditions such as bowel related diseases, autoimmune diseases, allergies, cancers, type 2 diabetes, obesity, depression, anxiety, and many others. For this reason, there has been an increased interest in understanding the role of the gut mucosal barrier dysfunction in the pathogenesis of many conditions targeting the gastrointestinal tract (GI) in mammals.

Under normal conditions, the gut mucosal barrier acts as a selective barrier permitting the absorption of nutrients, electrolytes and water and preventing the exposure to detrimental macromolecules, micro-organisms, dietary and microbial antigens (e.g. food allergens). The gut mucosal barrier is essentially composed of a layer of mucus and an underlying layer epithelial cells (referred to herein as 'gut epithelial cells'). The gut epithelial cells are tightly linked to each other by so-called 'tight junctions', which are basically 'physical joints' between the membranes of two gut epithelial cells. Maintenance of the gut mucosal barrier, particularly maintenance of the physical integrity of the gut epithelial cell layer (i.e. keeping the junctions between cell tight), is crucial for protection of the host against the migration of pathogenic micro-organisms, antigens, and other undesirable agents from the intestine to the blood stream.

The gut mucosal barrier is also heavily colonized by approximately $10^{12}$-$10^{14}$ commensal microorganisms, mainly anaerobic or microaerophilic bacteria, most of which live in symbiosis with their host. These bacteria are beneficial to their host in many ways. They provide protection against pathogenic bacteria and serve a nutritional role in their host by synthesizing vitamin K and some of the components of the vitamin B complex. Further, the gut mucosal barrier has evolved a complex 'gut mucosal immune system' for distinguishing between commensal (i.e. beneficial bacteria) and pathogenic bacteria and other detrimental agents. The gut mucosal immune system is an integral part of the gut mucosal barrier, and comprises lymphoid tissues and specialized immune cells (i.e. lymphocytes and plasma cells), which are scattered widely throughout the gut mucosal barrier. One of the microorganisms that naturally colonizes the mucosa of healthy subjects is the mucin-degrading *Akkermansia muciniphila*, which has been shown to increase the intestinal barrier function (Everard et al., PNAS 110 (2013) 9066-71; Reunanen et al., Appl Environ Microbiol Mar. 20, 2015), and thereby impact diseases associated with impaired gut barrier function.

Under certain circumstances, the gut mucosal barrier may be vulnerable to a wide variety of infectious organisms or agents, which are normally not able to cross the mucosal gut barrier but nevertheless manage to cross it (e.g. through gaps resulting from loose tight junctions between gut epithelia cells). Organisms or other agents that cross the gut mucosal barrier may cause diseases or other undesirable conditions (e.g. allergies) in the host. Examples of such diseases include obesity, metabolic syndrome, insulin-deficiency or insulin-resistance related disorders, type 2 diabetes, type 1 diabetes, inflammatory bowel disease (IBD), irritable bowel syndrome (IBS), glucose intolerance, abnormal lipid metabolism, atherosclerosis, hypertension, cardiac pathology, stroke, non-alcoholic fatty liver disease, alcoholic fatty liver disease, hyperglycemia, hepatic steatosis, dyslipidaemias, dysfunction of the immune system associated with obesity (weight gain), allergy, asthma, autism, parkinson's disease, multiple sclerosis, neurodegenerative diseases, depression, other diseases related to compromised barrier function, wound healing, behavioural disorders, alcohol dependence, cardiovascular diseases, high cholesterol, elevated triglycerides, atherosclerosis, sleep apnoea, osteoarthritis, gallbladder disease, and cancer.

Conversely, diseases such as those mentioned above as well as other conditions such as food allergies, immaturity of the gut, e.g., due to a baby being born prematurely, exposure to radiation, chemotherapy and/or toxins, autoimmune disorders, malnutrition, sepsis, and the like, may alter the physical integrity of the gut mucosal barrier (i.e. cause loosening of the tight junctions between the gut epithelial cells), which in turn may allow undesirable micro-organism or other agents to cross the host gut mucosal barrier.

Several vaccines and/or antibodies targeted against such micro-organisms or agents have been developed over the years. However, the success of such approach is mitigated as several micro-organisms or agents cannot be effectively targeted or eradicated with vaccines or antibodies.

Other approaches, which aim at preventing detrimental micro-organisms and other agents to cross the host's gut mucosal barrier in the first place and/or aim at preventing hyperpermeability of the gut mucosal barrier, have also been explored. For instance, compositions comprising glutamic acid have been developed to prevent and/or treat conditions associated with hyperpermeability of the gut mucosal barrier (WO 01/58283). Other substances including spermine and spermidine and precursors thereof, have also been used for the same purpose (Dorhout et al (1997). British J. Nutrition, pages 639-654). Preparations comprising arabinoxylan for promoting beneficial effects on the GI bacteria living in the vicinity of the gut mucosal barrier, have also been developed for the purpose of modulating the gut mucosal barrier (US2012/0230955).

It is an object of the present invention to provide agents and/or compositions comprising such agents, which are suitable for maintaining and/or restoring and/or increasing the physical integrity of the gut mucosal barrier and/or preventing hyperpermeability of the gut mucosal barrier in a mammal (e.g. human), and/or for maintaining and/or restoring and/or improving glucose and/or cholesterol and/or triglyceride homeostasis in a mammal, and preferably thereby prevent or treat diseases or conditions that are associated with suboptimal permeability of the gut mucosal barrier and/or glucose and/or cholesterol and/or triglyceride homeostasis imbalance in said mammal. Alternatively or additionally, it is an object of the present invention to provide agents and/or compositions comprising such agents, which are suitable for modulating and/or promoting the gut mucosal immune system function in a mammal.

SUMMARY OF THE INVENTION

The present invention is concerned with a composition comprising a polypeptide comprising the amino acid sequence of SEQ ID NO: 1 or an amino acid sequence comprising at least 50% sequence identity to the amino acid sequence of SEQ ID NO:1 over the entire length, said polypeptide being capable of effecting immune signaling and/or affecting intestinal barrier function and/or affecting glucose and/or cholesterol and/or triglyceride homeostasis, and a pharmaceutically or alimentarily acceptable carrier.

The composition may be a nutritional composition or a pharmaceutical composition.

The invention is also related to a genetically modified host cell wherein a nucleic acid molecule selected from the group of: a) a nucleic acid molecule comprising a nucleic acid sequence having at least 50% sequence identity with SEQ ID NO: 2 over the entire length; and b) a nucleic acid molecule comprising a nucleic acid sequence that encodes a polypeptide comprising the amino acid sequence of SEQ ID NO: 1 or an amino acid sequence comprising at least 50% sequence identity to the amino acid sequence of SEQ ID NO:1 over the entire length, said polypeptide being capable of effecting immune signaling and/or affecting intestinal barrier function and/or affecting glucose and/or cholesterol and/or triglyceride homeostasis, is introduced into its genome.

Additionally, the invention is directed to a genetically modified host cell, said host cell not being of the species *Akkermansia muciniphilla*, comprising a nucleic acid molecule selected from the group of: a) a nucleic acid molecule comprising nucleic acid sequence having at least 50% sequence identity with SEQ ID NO: 2 over the entire length; and b) a nucleic acid molecule comprising a nucleic acid sequence that encodes a polypeptide comprising the amino acid sequence of SEQ ID NO: 1 or an amino acid sequence comprising at least 50% sequence identity to the amino acid sequence of SEQ ID NO:1 over the entire length, said polypeptide being capable of effecting immune signaling and/or affecting intestinal barrier function and/or affecting glucose and/or cholesterol and/or triglyceride homeostasis.

The invention further provides a genetically modified host cell, said host cell being of the species *Akkermansia muciniphila*, wherein a nucleic acid molecule selected from the group of: a) a nucleic acid molecule comprising a nucleic acid sequence having at least 50% sequence identity with SEQ ID NO: 2 over the entire length; and b) a nucleic acid molecule comprising a nucleic acid sequence that encodes a polypeptide comprising the amino acid sequence of SEQ ID NO: 1 or an amino acid sequence comprising at least 50% sequence identity to the amino acid sequence of SEQ ID NO:1 over the entire length, said polypeptide being capable of effecting immune signaling and/or affecting intestinal barrier function and/or affecting glucose and/or cholesterol and/or triglyceride homeostasis, is introduced into its genome.

The invention further pertains to a method for producing a polypeptide comprising the amino acid sequence of SEQ ID NO: 1 or an amino acid sequence comprising at least 50% sequence identity to the amino acid sequence of SEQ ID NO:1 over the entire length, said polypeptide being capable of effecting immune signaling and/or affecting intestinal barrier function and/or affecting glucose and/or cholesterol and/or triglyceride homeostasis, comprising the steps of: a) culturing a host cell according to any of claims 3-5 under conditions permitting production of said polypeptide; and b) optionally, isolating the polypeptide produced in step (a).

The invention further provides for a polypeptide comprising the amino acid sequence of SEQ ID NO: 1 or an amino acid sequence comprising at least 50% sequence identity to the amino acid sequence of SEQ ID NO:1 over the entire length, said polypeptide being capable of effecting immune signaling and/or affecting intestinal barrier function and/or affecting glucose and/or cholesterol and/or triglyceride homeostasis, a host cell as taught herein, or a composition as taught herein, for use as a medicament, particularly for use in promoting gut mucosal immune system function, for maintaining, restoring and/or improving glucose and/or cholesterol and/or triglyceride homeostasis, or for maintaining, restoring and/or increasing the physical integrity of the gut mucosal barrier in a mammal.

Said polypeptide, composition or host cell may be for use in preventing and/or treating a disorder selected from the group consisting of obesity, metabolic syndrome, insulin-deficiency or insulin-resistance related disorders, type 2 diabetes, type 1 diabetes, gestational diabetes, preeclampsia, inflammatory bowel disease (IBD), irritable bowel syndrome (IBS), glucose intolerance, abnormal lipid metabolism, atherosclerosis, hypertension, cardiac pathology, stroke, non-alcoholic fatty liver disease, alcoholic fatty liver disease, hyperglycemia, hepatic steatosis, dyslipidaemias, dysfunction of the immune system associated with obesity (weight gain), allergy, asthma, autism, parkinson's disease, multiple sclerosis, neurodegenerative diseases, depression, other diseases related to compromised barrier function, wound healing, behavioural disorders, alcohol dependence, cardiovascular diseases, high cholesterol, elevated triglycerides, atherosclerosis, sleep apnea, osteoarthritis, gallbladder disease, cancer, and conditions altering the physical integrity of the gut mucosal barrier such as food allergies, immaturity of the gut, e.g., due to a baby being born prematurely, exposure to radiation, chemotherapy and/or toxins, autoimmune disorders, malnutrition, sepsis, and the like, in a mammal.

Alternatively or additionally, said polypeptide, host cell or composition may be for use in promoting anti-inflammatory activity in the gut of a mammal, and/or for use in promoting weight loss in a mammal.

The invention also relates to a method for treating and/or preventing a disorder selected from the group of obesity, metabolic syndrome, insulin-deficiency or insulin-resistance related disorders, type 2 diabetes, type 1 diabetes, gestational diabetes, preeclampsia, inflammatory bowel disease (IBD), irritable bowel syndrome (IBS), glucose intolerance, abnormal lipid metabolism, atherosclerosis, hypertension, cardiac pathology, stroke, non-alcoholic fatty liver disease, alcoholic fatty liver disease, hyperglycemia, hepatic steatosis, dyslipidaemias, dysfunction of the immune system associated with obesity (weight gain), allergy, asthma, autism, parkinson's disease, multiple sclerosis, neurodegenerative diseases, depression, other diseases related to compromised barrier function, wound healing, behavioural disorders, alcohol dependence, cardiovascular diseases, high cholesterol, elevated triglycerides, atherosclerosis, sleep apnoea, osteoarthritis, gallbladder disease, cancer, and conditions altering the physical integrity of the gut mucosal barrier such as food allergies, immaturity of the gut, e.g., due to a baby being born prematurely, exposure to radiation, chemotherapy and/or toxins, autoimmune disorders, malnutrition, sepsis, and the like, in a mammal, for promoting weight loss in a mammal, for promoting anti-inflammatory activity in the gut of a mammal, for promoting gut mucosal immune system function in a mammal, for maintaining, restoring and/or improving glucose and/or cholesterol and/or triglyceride homeostasis in a mammal, or for maintaining, restoring and/or increasing the physical integrity of the mucosal gut barrier of a mammal, comprising the step of administering to a mammal in need thereof, an effective amount of a polypeptide comprising the amino acid sequence of SEQ ID NO: 1 or an amino acid sequence comprising at least 50% sequence identity to the amino acid sequence of SEQ ID NO:1 over the entire length, said polypeptide being capable of effecting immune signaling and/or affecting intestinal barrier function and/or affecting glucose and/or cholesterol and/or triglyceride homeostasis, a host cell as taught herein, or a composition as taught herein.

The invention further pertains to a method for producing a polypeptide comprising the amino acid sequence of SEQ ID NO: 1 or an amino acid sequence comprising at least 50% sequence identity to the amino acid sequence of SEQ ID NO:1 over the entire length, said polypeptide being capable of effecting immune signaling and/or affecting intestinal barrier function and/or affecting glucose and/or cholesterol and/or triglyceride homeostasis, comprising the steps of: a) culturing bacteria of the species *Akkermansia muciniphila* in a suitable culture medium; and b) optionally, isolating the polypeptide produced in step (a).

General Definitions

In the context of the present invention, the term "polypeptide" is equivalent to the term "protein". A polypeptide has a particular amino acid sequence. A "variant" of the polypeptide of the present invention preferably has an amino acid sequence that has at least 50% sequence identity to the polypeptide of the present invention. A polypeptide of the invention is isolated when it is no longer in its natural environment, i.e., when it is no longer present in the context of fimbriae, and/or no longer present in the context of a cell, such as an *Akkermansia muciniphila* cell.

The term 'sequence identity' or 'sequence similarity' as used herein refer to a situation where an amino acid or a nucleic acid sequence has sequence identity or sequence similarity with another reference amino acid or nucleic acid sequence. 'Sequence identity' or 'sequence similarity' can be determined by alignment of two polypeptides or two nucleotide sequences using global or local alignment algorithms. Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimises the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or EmbossWin version 2.10.0 (using the program "needle"). Alternatively percent similarity or identity may be determined by searching against databases, using algorithms such as FASTA, BLAST, etc. Preferably, the sequence identity refers to the sequence identity over the entire length of the sequence.

'Transepithelial resistance' (abbreviated as TER) is a measure of the permeability of an epithelial cell layer in vitro. Increased epithelial permeability has been linked to weakening of the tight junctions, and with decrease of TER.

The term 'chimeric gene' as used herein refers to any non-naturally occurring gene, i.e., a gene which is not normally found in nature in a species, in particular a gene in which one or more parts of the nucleic acid sequence are not associated with each other in nature. For example, the promoter is not associated in nature with part or all of the transcribed region or with another regulatory region. The term 'chimeric gene' is understood to include expression constructs in which a heterologous promoter or transcription regulatory sequence is operably linked to one or more coding sequences, and optionally a 3'-untranslated region (3'-UTR). Alternatively, a chimeric gene may comprise a promoter, coding sequence and optionally a 3'-UTR derived from the same species, but that do not naturally occur in this combination.

The term 'genetically modified host cell' as used herein refers to cells that have been genetically modified, e.g. by the introduction of an exogenous nucleic acid sequence (e.g. SEQ ID NO:2 as taught herein) or by specific alteration of an endogenous gene sequence. Such cells may have been genetically modified by the introduction of, e.g., one or more mutations, insertions and/or deletions in the endogenous gene and/or insertion of a genetic construct (e.g. vector, or chimeric gene) in the genome. Genetically modified host cells may refer to cells in isolation or in culture. Genetically modified cells may be 'transduced cells', wherein the cells have been infected with for instance a modified virus, e.g., a retrovirus may be used but other suitable viruses may also be contemplated such as lentiviruses. Non-viral methods may also be used, such as transfections. Genetically modified host cells may thus also be 'stably transfected cells' or 'transiently transfected cells'. Transfection refers to non-viral methods to transfer DNA (or RNA) to cells such that a gene is expressed. Transfection methods are widely known in the art, such as calcium-phosphate transfection, PEG transfection, and liposomal or lipoplex transfection of nucleic acids, and the like. Such a transfection may be transient, but may also be a stable transfection, wherein cells that have integrated the gene construct into their genome may be selected.

The term 'effective amount' as used herein refers to an amount necessary to achieve an effect as taught herein. For instance, an effective amount of the polypeptide or genetically engineered host cell as taught herein, is an amount which is effectively useful for modulating and/or promoting the gut mucosal immune system function and/or maintaining and/or restoring and/or increasing the physical integrity of the gut mucosal barrier (e.g., promoting formation of tighter junction between the gut epithelium cells), and/or for modulating and/or stimulating the toll-like receptor signaling pathway (i.e. TLR2 pathway) in an immune cell and/or for increasing cytokine production (e.g. IL-6, IL-8, and IL-10) in an immune cell, and/or for preventing and/or treating disorders or conditions such as obesity, metabolic syndrome, insulin-deficiency or insulin-resistance related disorders, type 2 diabetes, type 1 diabetes, inflammatory bowel disease (IBD), irritable bowel syndrome (IBS), glucose intolerance, abnormal lipid metabolism, atherosclerosis, hypertension, cardiac pathology, stroke, non-alcoholic fatty liver disease, alcoholic fatty liver disease, hyperglycemia, hepatic steatosis, dyslipidaemias, dysfunction of the immune system associated with obesity (weight gain), allergy, asthma, autism, parkinson's disease, multiple sclerosis, neurodegenerative diseases, depression, other diseases related to compromised barrier function, wound healing, behavioural disorders, alcohol dependence, cardiovascular diseases, high cholesterol, elevated triglycerides, atherosclerosis, sleep apnoea, osteoarthritis, gallbladder disease, cancer, and conditions altering the physical integrity of the gut mucosal barrier such as food allergies, immaturity of the gut, e.g., due to a baby being born prematurely, exposure to radiation, chemotherapy and/or toxins, autoimmune disorders, malnutrition, sepsis, and the like.

The term 'physiologically-acceptable carrier' or 'alimentarily acceptable carrier', 'nutritionally acceptable carrier' or 'pharmaceutically-acceptable carrier' as used herein refers to a physiologically-acceptable or alimentarily acceptable carrier or nutritionally-acceptable or pharmaceutically-acceptable carrier material, such as a liquid or solid filler, diluent, excipient, solvent or encapsulating material, involved in providing an administration form of the polypeptide or host cell of the invention. Each carrier must be "acceptable" in the sense of being compatible with the other ingredients of the composition and not injurious to the subject, i.e. which are suitable for consumption or nutritionally acceptable. The term 'suitable for consumption' or 'nutritionally acceptable' refers to ingredients or substances, which are generally regarded as safe for human (as well as other mammals) consumption. Non-limiting examples of materials, which can serve as physiologically-acceptable carriers or nutritionally-acceptable or pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) other non-toxic compatible substances employed in pharmaceutical formulations, and the like. Further, the terms 'nutritionally-acceptable' and 'pharmaceutically acceptable' as used herein refer to those compositions or combinations of agents, materials, or compositions, and/or their dosage forms, which are within the scope of sound medical judgment, suitable for use in contact with the tissues of human beings and animals without excessive toxicity, irritation, allergic response, or other problem or complication, commensurate with a reasonable benefit/risk ratio.

The term "homeostasis" refers to the property of a system in which variables are regulated so that internal conditions remain stable and relatively constant. All animals regulate their blood glucose concentration. Glucose regulation in the body is a process of keeping the body in "glucose homeostasis". Mammals regulate their blood glucose with different hormones (e.g., insulin, glucagon, Glucagon like peptide 1, catecholamine and many others), and different nervous routes (e.g, nervous relay, gut to brain to peripheral organ axis). The human body maintains glucose levels constant most of the day, even after a 24-hour fast. Even during long periods of fasting, glucose levels are reduced only very slightly. Insulin, secreted by the beta cells of the pancreas, effectively transports glucose to the body's cells by instructing those cells to keep more of the glucose for their own use. If the glucose inside the cells is high, the cells will convert it to the insoluble glycogen to prevent the soluble glucose from interfering with cellular metabolism. Ultimately this lowers blood glucose levels, and insulin helps to prevent hyperglycemia. When insulin is deficient or cells become resistant to it, diabetes occurs. Glucagon, secreted by the alpha cells of the pancreas, encourages cells to break down stored glycogen or convert non-carbohydrate carbon sources to glucose via gluconeogenesis, thus preventing hypoglycemia. Numerous other factors and hormones are involved in the control of glucose metabolism (e.g., Glucagon like peptide 1, catecholamine and many others). Different mechanisms involving nervous routes are also contributing to this complex regulation.

"Cholesterol homeostasis" is a mechanism that contributes to the process of maintaining a balanced internal state of cholesterol within a living organism. Cholesterol, an essential biological molecule in the human body system, performs various physiological functions such as acting as a precursor for the production of bile acids, vitamin D, and steroid hormones. It also functions as a critical structural element in the cell membrane of every cell present in the body. Despite cholesterol's beneficial and necessary functions, an upset in cholesterol homeostasis can cause an increased risk of heart disease as well as upsetting other homeostatic feedback systems associated with cholesterol metabolism. The most conspicuous organ that controls cholesterol homeostasis is the liver because it not only biosynthesizes cholesterol released into the circulatory system, but breaks down potentially harmful, free-floating cholesterol from the bloodstream. HDLs are beneficial in maintaining cholesterol homeostasis because they pick up and deliver potentially dangerous cholesterol directly back to the liver where it is synthesized into harmless bile acids used by the digestive system. LDLs operate less beneficially because they tend to deposit their cholesterol in body cells and on arterial walls. It is excessive levels of LDLs that have been shown to increase risk for cardiovascular disease. In healthy subjects, cholesterol homeostasis is tightly regulated by complex feedback loops. In this case, if the healthy subject eats copious amounts of dietary cholesterol, biosynthesis in the liver is greatly reduced to keep balance. In a healthy subject who has a high baseline LDL level, either from years of poor diet habits or other genetic or medical conditions, the feedback loop and systemic coping mechanism may be overwhelmed by the same copious intake, causing dangerous homeostatic imbalance.

"Triglyceride homeostasis" is a mechanism that contributes to the process of maintaining a balanced internal state of triglycerides within a living organism. Triglyceride metabolism is of great clinical relevance. Hypertriglyceridemia denotes high (hyper-) blood or serum levels (-emia) of triglycerides, the most abundant fatty molecules. Elevated levels of triglycerides are associated with atherosclerosis, even in the absence of hypercholesterolemia (high cholesterol levels), and predispose to cardiovascular disease. High triglyceride levels also increase the risk of acute pancreatitis. Additionally, elevations and increases in TG levels over time enhance the risk of developing diabetes. It has been shown that insulin resistance is associated with high levels of triglycerides (TGs).

The term 'about', as used herein indicates a range of normal tolerance in the art, for example within 2 standard deviations of the mean. The term 'about' can be understood as encompassing values that deviate at most 10%, 9%, 8%, 7%, 6%, 5%, 4%, 3%, 2%, 1%, 0.5%, 0.1%, 0.05%, or 0.01% of the indicated value.

The terms 'comprising' or 'to comprise' and their conjugations, as used herein, refer to a situation wherein said terms are used in their non-limiting sense to mean that items following the word are included, but items not specifically mentioned are not excluded. It also encompasses the more limiting verb 'to consist essentially of' and 'to consist of'.

Reference to an element by the indefinite article 'a' or 'an' does not exclude the possibility that more than one of the elements is present, unless the context clearly requires that there be one and only one of the elements. The indefinite article 'a' or 'an' thus usually means 'at least one'.

DETAILED DESCRIPTION

The inventors have found that the polypeptide Amuc-1100, or variants thereof as taught herein, are capable of modulating and/or promoting the gut immune system function and/or maintaining and/or restoring and/or increasing the physical integrity of the gut mucosal barrier, and/or of maintaining and/or restoring and/or improving glucose and/or cholesterol and/or triglyceride homeostasis in a mammal (e.g. human). The inventors also found that this polypeptide is present outside the cells encoded by *Akkermansia muciniphila* supporting its role in signalling.

Without wishing to be bound by any theories, it is believed that such beneficial effects result from the ability of the polypeptides of the invention to interact with the TLR2 signalling pathway present at the surface of immune cells located in the vicinity of the gut mucosal barrier of a mammal. More specifically, the present inventors found that the polypeptides as taught herein are capable of interacting with to the TLR2 present at the surface of an immune cell and/or modulating and/or stimulating the TLR2-signaling pathway in an immune cell located in the vicinity of the gut mucosal barrier, so as to stimulate the secretion of cytokines (e.g. IL-6, IL-8, and IL-10) from said immune cells.

Further, the present inventors found that the polypeptides, including variants thereof, as taught herein, are capable of modulating and/or increasing the transepithelial resistance of the gut mucosal barrier of a mammal. Since increased transepithelial resistance measurement serves as an index of decreased permeability of the gut mucosal barrier, it is believed that the polypeptides, including variants thereof, as taught herein are capable of modulating the physical integrity of the gut mucosal barrier, particularly at the level of the tight junctions between epithelial cells.

Combined together, these effects are believed to result in an improved or increased gut mucosal immune system function (e.g. greater release of cytokines at the gut mucosal barrier) as well as improved or increased physical integrity of the gut mucosal barrier, particularly at the level of the connection between gut epithelial cells (i.e. via tighter tight junctions between cells).

Additionally, it was found that treatment of HFD-fed mice with Amuc-1100 caused a prominent decrease in body weight and fat mass gain without affecting food intake. Treatment with Amuc-1100 also corrected the HFD-induced hypercholesterolemia, with a significant decrease in serum HDL-cholesterol and a similar trend for LDL-cholesterol. Further, administration of Amuc-1100 reduced glucose intolerance with the same potency as the live *Akkermansia muciniphila* bacterium.

Finally, it is known that metformin stimulates the growth of *Akkermansia* (Lee H and Ko G, A ppl Environ Microbiol. 2014 October; 80(19):5935-43) and hence it is likely that *Akkermansia* and its extracellular peptides such as Amuc-1100 may have a similar effect as metformin on gestational diabetes and on preeclampsia (Syngelaki et al. N Engl J Med. 2016 Feb. 4; 374(5):434-43).

Polypeptides

The present disclosure teaches an isolated polypeptide comprising the amino acid sequence of SEQ ID NO: 1 or an amino acid sequence comprising at least 50% amino acid sequence identity to the amino acid sequence of SEQ ID NO:1 over the entire length, said polypeptide being capable of effecting immune signalling and/or affecting intestinal barrier function and/or affecting glucose and/or cholesterol homeostasis. The polypeptide taught herein may be capable of binding to the toll like receptor 2 (TLR2).

In one embodiment, the polypeptides and variants thereof as taught herein are capable of stimulating the TLR2 signalling pathway in a cell, stimulating the release of cytokines from a cell (e.g. IL-6, IL-8, IL-10 and the like) and/or increasing transepithelial resistance (TER) of mammalian, e.g., human, cells, and/or improving the metabolic or immune status of a mammal, e.g., mouse or human.

The polypeptide taught herein may also be referred to as 'Amuc-1100 protein' or 'Amuc-1100 polypeptide'. It is to be understood that the term 'Amuc-1100 protein' or 'Amuc-1100 polypeptide' or 'polypeptide as taught herein' also includes variants of the Amuc-1100 protein having the amino acid sequence of SEQ ID NO:1, the amino acid sequences of said variants having more than 50%, preferably more than 55%, more than 60%, more than 65%, more than 70%, preferably more than 75%, more than 80%, more than 85%, more than 90%, more than 95%, preferably more than 96%, preferably more than 97%, preferably more than 98%, and preferably more than 99% sequence identity with the amino acid sequence of SEQ ID NO:1. Variants of the Amuc-1100 polypeptide having the amino acid sequence of SEQ ID NO:1 also include polypeptides, which have been derived, by way of one or more amino acid substitutions, deletions or insertions, from the polypeptide having the amino acid sequence of SEQ ID NO:1. Preferably, such polypeptides comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions as compared to the polypeptide having the amino acid sequence of SEQ ID NO:1.

The polypeptide as taught herein may be preceded by a N terminal signal sequence stimulating secretion of the polypeptide from the cell. In an embodiment, the N terminal signal sequence may be a polypeptide comprising the amino acid sequence of SEQ ID NO:3, which is the predicted naturally occurring N terminal signal sequence of the Amuc-1100 polypeptide. However, other N terminal signal sequences capable of allowing Amuc-1100 to be secreted from a cell may also be employed. For example, a truncated version or expanded version of the predicted naturally occurring N terminal signal sequence of the Amuc-1100 polypeptide may be employed, as long as such N terminal signal sequence is capable of allowing Amuc-1100 to be secreted from a cell. Alternatively, a non-naturally occurring N terminal signal sequence may be employed. The skilled person is capable of identifying N terminal signal sequences that are suitable for use in the present invention. Thus, a polypeptide of the present invention may comprise the amino acid sequence of SEQ ID NO:3 N terminal from its amino acid sequence.

Amino acid sequence identity may be determined by any suitable means available in the art. For instance, amino acid sequence identity may be determined by pairwise alignment using the Needleman and Wunsch algorithm and GAP default parameters as defined above. It is also understood that many methods can be used to identify, synthesize or isolate variants of the polypeptides as taught herein, such as western blot, immunohistochemistry, ELISA, amino acid synthesis, and the like.

It is also understood that any variants of the Amuc-1100 polypeptides as taught herein exert the same function and/or have the same activity as the polypeptide Amuc-1100 as taught herein. The functionality or activity of any Amuc-1100 polypeptides or variants thereof may be determined by any known methods in the art, which the skilled person would consider suitable for these purposes.

Polynucleotides

The present disclosure also teaches a nucleic acid molecule, such as an isolated, synthetic or recombinant nucleic acid molecule, comprising a nucleic acid sequence selected from the group of:
(a) a nucleic acid sequence having at least 50% sequence identity with SEQ ID NO: 2 over the entire length; and
(b) a nucleic acid sequence that encodes the polypeptide as taught herein.

The term "isolated nucleic acid molecule" (e.g. cDNA, genomic DNA or RNA) includes naturally occurring, artificial or synthetic nucleic acid molecules. The nucleic acid molecules may encode any of the polypeptides as taught herein. Said nucleic acid molecule may be used to produce the polypeptides as taught herein. Due to the degeneracy of the genetic code various nucleic acid molecules may encode the same polypeptide (e.g. a polypeptide comprising the amino acid sequence of SEQ ID NO:1).

In an embodiment, the isolated nucleic acid molecules as taught herein include any variant nucleic acid molecules, which encompass any nucleic acid molecules comprising a nucleotide sequence having more than 50%, preferably more than 55%, preferably more than 60%, preferably more than 65%, preferably more than 70%, preferably more than 75%, preferably more than 80%, preferably more than 85%, preferably more than 90%, preferably more than 95%, preferably more than 96%, preferably more than 97%, preferably more than 98%, and preferably more than 99% sequence identity with the nucleic acid sequence of SEQ ID NO:2. Variants also include nucleic acid molecules, which have been derived, by way of one or more nucleic acid substitutions, deletions or insertions, from the nucleic acid molecule having the nucleic acid sequence of SEQ ID NO:2. Preferably, such nucleic acid molecules comprise from 1, 2, 3, 4, 5, 6, 7, 8, 9, 10 or more up to about 100, 90, 80, 70, 60, 50, 45, 40, 35, 30, 25, 20, 15 nucleic acid substitutions, deletions or insertions as compared to SEQ ID NO:2.

Sequence identity may be determined by any suitable means available in the art. For instance, bioinformatics may be used to perform pairwise alignment between nucleic sequences to identify regions of similarity that may be due to functional, structural, or evolutionary relationships between the sequences. It is also understood that many methods can be used to identify, synthesize or isolate variants of the polynucleotide as taught herein, such as nucleic acid hybridization, PCR technology, in silico analysis and nucleic acid synthesis, and the like.

It is further understood that any nucleic acid molecule as taught herein may encode a polypeptide as taught herein.

In an embodiment, the nucleic acid molecule is a nucleic acid molecule having the nucleic acid sequence as set forth in SEQ ID NO:2.

Alternatively, the isolated nucleic acid molecule may be a nucleic acid molecule that hybridizes under stringent conditions with the nucleic acid molecules as taught herein and encoding a polypeptide as taught herein. For instance, such nucleic acid sequence may be advantageously used in screening assays aimed to detect the presence or absence of any homologs of the nucleic acid molecules of the invention in a cell or in an organism or to detect a decreases or increase in the expression of the nucleic acid molecules as taught herein, in a cell or in an organism.

The nucleic acid molecule as taught herein may encompass a nucleic acid molecule encoding a N terminal signal sequence that is suitable for stimulating secretion of the polypeptide as taught herein from its host cell. Said N terminal signal sequence encoding nucleic acid molecule may comprise the nucleic acid sequence as set forth in SEQ ID NO:4.

In an embodiment, the nucleic acid molecule as taught herein may be comprised in a chimeric gene, wherein said nucleic acid molecule is operably linked to a promoter. Thus the present inventions also relates to a chimeric gene comprising the nucleic acid molecule as taught herein.

Any promoters known in the art, and which are suitable for linkage with the nucleic acid molecules as taught herein may be used. Non-limiting examples of suitable promoters include promoters allowing constitutive or regulated expression, weak and strong expression, and the like. Any known methods in the art may be used to include the nucleic acid molecule as taught herein in a chimeric gene.

It may be advantageous to operably link the nucleic acid molecule as taught herein to a so-called 'constitutive promoter'.

Alternatively, it may be advantageous to operably link the polynucleotides and variants thereof as taught herein to a so-called 'inducible promoter'. An inducible promoter may be a promoter that is physiologically (e.g. by external application of certain compounds) regulated.

The chimeric gene as taught herein may be comprised in a 'vector' or 'nucleic acid construct'. Thus the present invention also related to vectors comprising the chimeric gene as taught herein or the nucleic acid molecule as taught herein.

In an aspect, the present invention relates to a host cell that has been genetically modified to comprise, e.g., in its genome, a nucleic acid molecule as taught herein, a chimeric gene as taught herein or a vectors as taught herein.

The genetically modified host cell as taught herein may be used to produce in vitro, ex vivo and/or in vitro, the polypeptides and variants thereof as taught herein within the host cell cytoplasm or released from the cells by any means. The polypeptides as taught herein may, in particular, be expressed as a soluble or secreted molecule. The genetically modified host cells as taught herein can be any host cells suitable for transformation procedures or genetic engineering procedures. Non-limiting examples of suitable host cells include cultivable cells, such as any prokaryotic or eukaryotic cells. In an embodiment, the AMUC-1100 polypeptide is expressed in bacteria, such as *Escherichia coli.*

In an embodiment, the host cell as taught herein may be any cell that naturally expresses the polypeptide or variant thereof taught herein. In such case, the host cell may overexpress the polypeptide or variant thereof as taught herein.

In yet an embodiment, the host cell as taught herein may be any cell that does not naturally express the polypeptide or variants thereof as taught herein.

In an embodiment, the host cell as taught herein does not belong to the species *Akkermansia muciniphila.*

In another embodiment, the host cell may belong to the species *Akkermansia muciniphila*, and is genetically modified to comprise additional copies of the nucleic acid molecules taught herein, or to comprise a chimeric gene or vector as taught herein. Such *Akkermansia muciniphila* cell may overexpress the Amuc-1100 polypeptide or a variant thereof taught herein.

The host cell as taught herein may be genetically modified using any known methods in the art. For instance, the host cells or organisms as taught herein may be genetically modified by a method comprising the step of
a) transforming the host cell with a nucleic acid molecule as taught herein, such as an isolated, synthetic or recombinant nucleic acid molecule comprising a nucleic acid sequence selected from the group of a nucleic acid sequence having at least 50% sequence identity with SEQ ID NO: 2 over the entire length; and a nucleic acid sequence capable of encoding the polypeptides and variants thereof as taught herein.
b) culturing said host cell under conditions suitable to allow expression of the nucleic acid molecule as taught herein and/or production of the polypeptide or a variant thereof as taught herein;
c) optionally, screening for host cells capable of expressing the nucleic acid molecule as taught herein and/or producing the polypeptide or a variant thereof as taught herein.

In a preferred embodiment, the host cells or organisms as taught herein may be transformed with a nucleic acid molecule having the nucleotide sequence of SEQ ID NO:2, or a variant thereof as taught herein.

In an embodiment, the genetically modified host cell as taught herein may belong to a species of bacteria that naturally occurs or lives in the vicinity of or within the gut mucosal barrier of a mammal. Said species of bacteria are often referred to as 'gut mucosal-associated bacteria species'. Non-limiting examples of 'gut mucosal-associated bacteria species' include *Akkermansia muciniphila* (ATTC BAA-835), *Faecalibacterium prausnitzii* (A2-165), *Lactobacillus rhamnosus* (ATCC 53103) and *Bifidobacterium breve* (DSM-20213).

In certain embodiments, it may be advantageous to genetically modify a gut mucosal-associated bacteria with any of the polynucleotides and variants thereof as taught herein, for instance to express or overexpress the polynucleotides as taught herein or to produce or overproduce the polypeptides as taught herein, directly into the vicinity of, or within the gut mucosal barrier of a mammal (e.g. human). In a preferred embodiment, the gut mucosal-associated bacteria may by any bacteria from the species *Akkermansia muciniphilla*. Such overproduction may be realized by genetic modification tools involving recombinant DNA technologies, genome editing such as by using tools based on CRISPR/cas-like systems, or by classical mutation selection systems.

In an embodiment, the genetically modified host cell may be any bacteria, particularly one which is not from a species of bacteria that naturally occurs or lives in the vicinity of or within the gut mucosal barrier of a mammal. Non-limiting examples of such bacteria include any beneficial isolated intestinal bacterial strains, e.g. probiotic bacteria, particularly strains selected from the genera *Lactococcus, Lactobacillus,* or *Bifidobacterium* may be used. In addition, strict anaerobic intestinal bacteria may be used such as those belonging to the genera known to occur in the human intestinal tract (Rajilic-Stojanovic & de Vos, The first 1000 cultured species of the human gastrointestinal microbiota. FEMS Microbiol Rev. 38: 996-1047).

Methods for Producing the Polypeptide

In a further aspect, the present invention relates to a method for producing the polypeptides, including variants, as taught herein, comprising the steps of:
(a) culturing a host cell as taught herein under conditions permitting production of the polypeptide or a variant thereof as taught herein; and
(b) optionally, isolating the polypeptide produced in step (a).

In step (a), the host cell as taught herein may be cultured according to any known culturing methods and on any known culture medium. The skilled person will be able to select a suitable host cell and will be able to establish suitable conditions allowing production of the polypeptide.

Alternatively, the polypeptide may be produced by a method comprising the steps of:
(a) culturing bacteria of the species *Akkermansia muciniphila* in a suitable culture medium; and
(b) optionally, isolating the polypeptide produced in step (a).

The polypeptide produced in steps (a) of the methods above may be isolated by any known methods in the art. The skilled person will be capable of isolating the polypeptide produced from such culture medium.

Suitable culture media are, for example, taught by Derrien et al. (2004, Int. J. Syst. Evol. Microbiol. 54: 1469-76). Derrien et al. teach that *A. muciniphila* strain Muc$^T$ was isolated and grown on a basal anaerobic medium containing hog gastric mucin as the sole carbon and nitrogen source. The authors also teach that *A. muciniphila* can be grown on rich media, such as Columbia Broth (CB) and Brain Heart Infusion (BHI) broth or basal medium with glucose and high concentrations of casitone and yeast-extract. Similarly, Lukovac et al. (mBio teaches the growth of *A. muciniphila* in a basal medium containing glucose and fucose, as well as high amounts of casitone (2014, mBio 01438-14)

Methods for Screening Bacteria

In further aspect, the present invention relates to a method for detecting the presence or absence, in a bacteria, of a polynucleotide as taught herein, comprising the step of:
(a) providing a nucleic acid molecule that is capable of hybridizing under stringent conditions to a nucleic acid molecule having the nucleic acid sequence of SEQ ID NO:2 or having a nucleic acid sequence comprising at least 50% sequence identity to the nucleic acid sequence of SEQ ID NO:2 over the entire length;
(b) detecting the nucleic acid molecule of step (a) to identify a bacteria comprising the nucleic acid molecule having the nucleic acid sequence of SEQ ID NO:2 or a nucleic acid sequence comprising at least 50% nucleic acid sequence identity to the nucleic acid sequence of SEQ ID NO:2 over the entire length.

The present disclosure also relates to a method for detecting the presence or absence, in a bacteria, of a polypeptide or variants thereof as taught herein, comprising the step of:
(a) providing an antibody that is capable of binding to a polypeptide comprising the amino acid sequence of SEQ ID NO:1 or an amino acid sequence comprising at least 50% sequence identity to the amino acid sequence of SEQ ID NO:1;
(b) detecting the antibody of step (a) to identify bacteria comprising a polypeptide having the amino acid sequence of SEQ ID NO:1 or an amino acid sequence comprising at least 50% sequence identity to the amino acid sequence of SEQ ID NO:1.

In an embodiment, the nucleic acid of step (a) and/or the antibody of step (c) are labelled (e.g. fluorescent, radioactive labels, etc.) to facilitate detection.

Compositions

In a further aspect, the present inventions relates to a composition comprising any of the polypeptides as taught herein. In a preferred embodiment, the polypeptide has the amino acid sequence of SEQ ID NO: 1.

In a yet further aspect, the present invention relates to a composition comprising a host cell as taught herein. The host cell may be present in an amount ranging from about $10^4$ to about $10^{15}$ colony forming units (CFU). For instance, an effective amount of the host cell may be an amount of about $10^5$ CFU to about $10^{14}$ CFU, preferably about $10^6$ CFU to about $10^{13}$ CFU, preferably about $10^7$ CFU to about $10^{12}$ CFU, more preferably about $10^8$ CFU to about $10^{12}$ CFU. The host cell may be viable or may be dead. The effectiveness of the host cell correlates with the presence of the polypeptide as taught herein.

In an embodiment, the composition as taught herein further comprises a carrier, e.g., a physiologically acceptable carrier or a pharmaceutically acceptable carrier or an alimentarily acceptable carrier or a nutritionally acceptable carrier. The carrier may be any inert carrier. For instance, non-limiting examples of suitable physiologically or pharmaceutically acceptable carriers include any of well-known physiological or pharmaceutical carriers, buffers, diluents, and excipients. It will be appreciated that the choice for a suitable physiological or pharmaceutical carrier or alimentary carrier or nutritional carrier will depend upon the intended mode of administration of the composition as taught herein (e.g., oral) and the intended form of the composition (e.g. beverage, yogurt, powder, capsules, and the like). The skilled person knows how to select a suitable carrier, e.g., physiologically acceptable carrier or a nutritionally acceptable carrier or a pharmaceutically acceptable carrier, which is suitable for or compatible with the compositions as taught herein.

In an embodiment, the compositions as taught herein may be a nutritional, or alimentary, composition. For instance, the composition as taught herein may be a food, food supplement, feed, or a feed supplement such as a dairy product, e.g., a fermented dairy product, such as a yogurt or a yogurt drink. In this case, the composition may comprise a nutritionally acceptable or alimentarily acceptable carrier, which may be a suitable food base.

In an embodiment, the compositions as taught herein may be a pharmaceutical composition. The pharmaceutical composition may also be for use as a supplement (e.g. food supplement). The pharmaceutical composition as taught herein may comprise a pharmaceutical, nutritionally or alimentarily or physiologically-acceptable carrier, in addition to the polypeptide as taught herein and/or host cells as taught herein. The preferred form will depend on the intended mode of administration and (therapeutic) application. The carrier may be any compatible, physiologically-acceptable, non-toxic substances suitable to deliver the polypeptide as taught herein and/or host cell as taught herein to the GI tract of a mammal (e.g. human), preferably in the vicinity of or within the gut mucosal barrier (more preferably the colon mucosal barrier) in a mammal. For example, sterile water, or inert solids may be used as a carrier, usually complemented with a pharmaceutically acceptable adjuvant, buffering agent, dispersing agent, and the like.

The composition as taught herein may be in liquid form, e.g. a stabilized suspension of the polypeptide as taught herein or host cell as taught herein, or in solid form, e.g., a powder of lyophilized host cells as taught herein. In case the host cells as taught herein are lyophilized, a cryoprotectant such as lactose, trehalose or glycogen may be employed. For oral administration, polypeptides as taught herein or lyophilized host cells as taught herein may be administered in solid dosage forms, such as capsules, tablets, and powders, or in liquid dosage forms, such as elixirs, syrups, and suspensions. The polypeptide as taught herein or host cell as taught herein may be encapsulated in capsules such as gelatin capsules, together with inactive ingredients and powder carriers, such as e.g. glucose, lactose, sucrose, mannitol, starch, cellulose or cellulose derivatives, magnesium stearate, stearic acid, sodium saccharin, talcum, magnesium carbonate and the like.

In an embodiment, the compositions as taught herein may comprise one or more ingredients, which are suitable for promoting survival and/or viability and/or maintaining the and/or integrity of the polypeptide as taught herein and/or the host cell as taught herein during storage and/or during exposure to bile and/or during passage through the GI tract of a mammal (e.g. a human). Non-limiting examples of such ingredients include an enteric coating, and controlled release agents allowing passage through the stomach. The skilled person knows how to select suitable ingredients for ensuring that the active component (be it a polypeptide or a host cell) receives its intended destination, where it exerts its action.

In an embodiment, the compositions as taught herein may further comprise a mucosal binding agent or mucosal binding polypeptide. The term 'mucosal binding agent' or 'mucosal binding polypeptide' as used herein refers to an agent or a polypeptide that is capable of attaching itself to the gut mucosal surfaces of the gut mucosal barrier of a mammal (e.g. human).

Alternatively, use can be made of specific docking systems to attach the Amuc-1100 polypeptide to Amuc-1100 producing cells or even non Amuc-1100-producing cells that are either alive or dead. The binding can be either at the C- or N-terminus, whatever seems to be most efficient, while also the use of spacer peptides has been described. Examples include the use of LysM-based peptidoglycan binding systems (Visweswaran G R et al. 2014, Appl Microbiol Biotechnol. 98:4331-45.). Moreover, a variety of mucosal binding polypeptides have been disclosed in the art. Non-limiting examples of mucosal binding polypeptide include bacterial toxin membrane binding subunits including such as the B subunit of cholera toxin, the B subunit of the *E. coli* heat-labile enterotoxin, *Bordetella pertussis* toxin subunits S2, S3, S4 and/or S5, the B fragment of Diphtheria toxin and the membrane binding subunits of Shiga toxin or Shiga-like toxins. Other suitable mucosal binding polypeptides include bacterial fimbriae proteins such as including *E. coli* fimbria K88, K99, 987P, F41, FAIL, CFAIII ICES1, CS2 and/or CS3, CFAIIV ICS4, CS5 and/or CS6), P fimbraiae, or the like. Other non-limiting examples of fimbriae include *Bordetella pertussis* filamentous hemagglutinin, *Vibrio cholerae* toxin-coregulate pilus (TCP), Mannose-sensitive hemagglutinin (MSHA), fucose-sensitive hemagglutinin (PSHA), and the like. Still other mucosal-binding agents include viral attachment proteins including influenza and sendai virus hemagglutinins and animal lectins or lectin-like molecules including immunoglobulin molecules or fragments thereof, calcium-dependant (C-type) lectins, selectins, collectins or helix pomatis hemagglutinin, plant lectins with mucosabinding subunits include concanavalin A, wheat-germ agglutinin, phytohemagglutinin, abrin, ricin and the like. The advantage of this delivery is that one obviates the use of a living recombinant organism.

Although not essential, it may be advantageous to add one or more mucosal binding agent or mucosal binding polypeptide to the composition as taught herein so as to target the polypeptide as taught herein or the host cell as taught herein to the gut mucosal barrier.

The compositions as taught herein may further comprise ingredients selected from the group consisting of prebiotics, probiotics, carbohydrates, polypeptides, lipids, vitamins, minerals, medicinal agents, preservative agents, antibiotics, or any combination thereof.

In one embodiment, the composition as taught herein may further comprise one or more ingredients, which further enhance the nutritional value and/or the therapeutic value the compositions as taught herein. For instance, it may be advantageous to add one or more ingredients (e.g. nutritional ingredients, veterinary or medicinal agents etc.) selected from proteins, amino acids, enzymes, mineral salts, vitamins (e.g. thiamine HCl, riboflavin, pyridoxine HCl, niacin, inositol, choline chloride, calcium pantothenate, biotin, folic acid, ascorbic acid, vitamin B12, p-aminobenzoic acid, vitamin A acetate, vitamin K, vitamin D, vitamin E, and the like), sugars and complex carbohydrates (e.g. water-soluble and water-insoluble monosaccharides, disaccharides, and polysaccharides), medicinal compounds (e.g. antibiotics), antioxidants, trace element ingredients (e.g. compounds of cobalt, copper, manganese, iron, zinc, tin, nickel, chromium, molybdenum, iodine, chlorine, silicon, vanadium, selenium, calcium, magnesium, sodium and potassium and the like). The skilled person is familiar with methods and ingredients that are suitable to enhance the nutritional and/or therapeutic/medicinal value of the compositions as taught herein.

In an embodiment, the host cell may be incorporated in lyophilized form, or microencapsulated form (reviewed by, for example, Solanki et al. BioMed Res. Int. 2013, Article ID 620719), or any other form preserving the activity and/or viability of the host cell (e.g. bacterial strain).

Methods of Treatment

In another aspect, the present invention relates to methods for treating and/or preventing a disorder or condition selected from the group of obesity, metabolic syndrome, insulin-deficiency or insulin-resistance related disorders, type 2 diabetes, type 1 diabetes, gestational diabetes, preeclampsia, inflammatory bowel disease (IBD), irritable bowel syndrome (IBS), glucose intolerance, abnormal lipid metabolism, atherosclerosis, hypertension, cardiac pathology, stroke, non-alcoholic fatty liver disease, alcoholic fatty liver disease, hyperglycemia, hepatic steatosis, dyslipidaemias, dysfunction of the immune system associated with obesity (weight gain), allergy, asthma, autism, parkinson's disease, multiple sclerosis, neurodegenerative diseases, depression, other diseases related to compromised barrier function, wound healing, behavioural disorders, alcohol dependence, cardiovascular diseases, high cholesterol, elevated triglycerides, atherosclerosis, sleep apnoea, osteoarthritis, gallbladder disease, cancer, and conditions altering the physical integrity of the gut mucosal barrier such as food allergies, immaturity of the gut, e.g., due to a baby being born prematurely, exposure to radiation, chemotherapy and/or toxins, autoimmune disorders, malnutrition, sepsis, and the like, in a mammal; methods for promoting weight loss in a mammal; methods for promoting anti-inflammatory activity in the gut of a mammal; methods for promoting gut mucosal immune system function in a mammal; methods for maintaining, restoring and/or improving glucose and/or cholesterol and/or triglyceride homeostasis; and methods for maintaining, restoring and/or increasing the physical integrity of the mucosal gut barrier in a mammal. The methods comprise the step of administering to a mammal in need thereof, an effective amount of a polypeptide as taught herein, a host cell as taught herein or a composition as taught herein.

In one embodiment, the polypeptide as taught herein, a host cell as taught herein or a composition as taught herein may be administered by any known methods of administration. For instance, the compositions as taught herein may be administered orally, intravenously, topically, enterally or parenterally. It is understood that the modes or routes of administration will depend on the case at hand (e.g. age of the subject, desired location of the effects, disease conditions and the like) as well as on the intended form of the composition (e.g. pill, liquid, powder etc.).

In a preferred embodiment, the polypeptide as taught herein, a host cell as taught herein or a composition as taught herein are administered orally.

Uses

In a further aspect, the present invention relates to the use of the nucleic acid molecule as taught herein, chimeric gene as taught herein and/or vectors as taught herein for producing the polypeptides as taught herein and/or for generating the host cells as taught herein. The polypeptide as taught herein and/or the host cell as taught herein may have enhanced ability to interact with the TLR2 receptor on a cell and/or may have an enhanced ability to stimulate TLR2 signalling pathway in a cell, and/or may have an enhanced ability to stimulate production of cytokines, particularly IL-1β, IL-6, IL-8, IL-10 and TNF-α, from a cell, and/or may have an enhanced ability to increase TER of mammalian, e.g., human, cells, as compared to a host cell (e.g. bacteria) not genetically modified with the polynucleotides, chimeric genes or vectors as taught herein.

In a further aspect, the present invention relates to the polypeptide as taught herein, host cells as taught herein or composition as taught herein for use as a medicament; particularly for use in promoting gut mucosal immune system function or for maintaining, restoring and/or increasing the physical integrity of the gut mucosal barrier in a mammal; for maintaining, restoring and/or improving glucose and/or cholesterol and/or triglyceride homeostasis in a mammal; for use in preventing and/or treating a disorder or condition selected from the group consisting of obesity, such as diet-induced obesity, metabolic syndrome, insulin-deficiency or insulin-resistance related disorders, type 2 diabetes, type 1 diabetes, gestational diabetes, preeclampsia, inflammatory bowel disease (IBD), irritable bowel syndrome (IBS), glucose intolerance, abnormal lipid metabolism, atherosclerosis, hypertension, cardiac pathology, stroke, non-alcoholic fatty liver disease, alcoholic fatty liver disease, hyperglycemia, hepatic steatosis, dyslipidaemias, dysfunction of the immune system associated with obesity (weight gain), allergy, asthma, autism, parkinson's disease, multiple sclerosis, neurodegenerative diseases, depression, other diseases related to compromised barrier function, wound healing, behavioural disorders, alcohol dependence, cardiovascular diseases, high cholesterol, elevated triglycerides, atherosclerosis, sleep apnoea, osteoarthritis, gallbladder disease, cancer, and conditions altering the physical integrity of the gut mucosal barrier such as food allergies, immaturity of the gut, e.g., due to a baby being born prematurely, exposure to radiation, chemotherapy and/or toxins, autoimmune disorders, malnutrition, sepsis, and the like, in a mammal; for use in promoting anti-inflammatory activity in the gut of a mammal; or for use in promoting weight loss in a mammal.

In an embodiment, the mammal, e.g., human, may be of any age group (e.g. infants, adults, elderly) and of any gender (male and female). In an embodiment, the mammal may be an infant (e.g. new-borns, babies, toddlers etc.), particularly an infant, which was born prematurely.

The mammal may be any mammal, for example, humans, non-human primates, rodents, cats, dogs, cow, horses, and the like. In a preferred embodiment, the mammal is a human being.

The present invention is further illustrated, but not limited, by the following examples. From the above discussion and these examples, one skilled in the art can ascertain the essential characteristics of the present invention, and without departing from the teaching and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

SEQUENCE LISTING

SEQ ID NO:1: Amino acid sequence of the Amuc-1100 polypeptide
SEQ ID NO: 2: Nucleotide sequence encoding the Amuc-1100 polypeptide
SEQ ID NO:3: Amino acid sequence of the predicted N-terminal signal sequence of Amuc-1100 polypeptide
SEQ ID NO:4: Nucleotide sequence of the predicted N-terminal signal sequence of Amuc-1100 polypeptide

EXAMPLES

Example 1: Generation of Bacteria Genetically Modified to Produce Amuc-1100 Proteins Method:
The polynucleotide encoding the mature Amuc-1100 (nucleotide sequence of SEQ ID NO:2) was cloned into E. coli TOP10 with a C-terminal His-Tag under control of the inducible T7 promoter of pET28-derivatives and introduced into E. coli BL23(DE3) for overproduction. For this purpose an ATG start codon was added to the nucleotide sequence of SEQ ID NO; 2, so that the resulting polypeptide started with the amino acid sequence MIVNS. All constructs were confirmed by Sanger sequence analysis. The constructs carrying the overexpressed Amuc-1100 resulted in overproduction of soluble Amuc-1100 proteins that were purified to apparent homogeneity by Ni-column affinity chromatography and used in a concentration of 100-300 ug/ml. The purified Amuc-1100 was used to generate antibodies in rabbits essentially as described previously (Reunanen J et al. 2012, Appl Environ Microbiol 78:2337-44).

Results:
The results show that E. coli transformed with the polynucleotide of the invention (SEQ ID NO:2) was able to produce the Amuc-1100 protein in a soluble form that could be isolated easily using Ni-column chromatography as described (Tailford L E et al. 2015, Nat Commun. 6:7624).

Example 2: Interaction and Stimulation of the TLR2 Signalling Pathway

Method:
In order to test the ability of Amuc-1100 to bind the TLR2 and other TLR receptors and subsequently stimulate the TLR2 and other TLR signalling pathways, reporter cell lines expressing TLR2 and TLR4 receptors were prepared. The ability of Amuc-1100 to bind cell lines expressing TLR2 or TLR4 and thereafter stimulate the TLR2 and/or TLR4 signaling pathway in said cells was tested in vitro by measuring the production of NK-kB from the reporter cells.

Briefly, hTLR2 and hTLR4 cell lines (Invivogen, CA, USA) were used. Stimulation of the receptors with the corresponding ligands activates NF-κB and AP-1, which induces the production of Secreted embryonic alkaline phosphatase (SEAP), the levels of which can be measured by spectrophotometer (Spectramax). All cell lines were grown and subcultured up 35 to 70-80% of confluency using as a maintenance medium Dulbecco's Modified Eagle Medium (DMEM) supplemented with 4.5 g/l D-glucose, 50 U/ml penicillin, 50 µg/ml streptomycin, 100 µg/ml Normocin, 2 mM L-glutamine, and 10% (v/v) of heat-inactivated Fetal Bovine Serum (FBS). For each cell line, an immune response experiment was carried out by adding 20 µl of Amuc-1100 suspensions. The reporter cells were incubated with Amuc-1100 for 20-24 h at 37° C. in a 5% CO2 incubator. Receptor ligands Pam3CSK4 (10 ng/ml for hTLR2) and LPS-EB (50 ng/ml for hTLR4) were used as positive control whereas maintenance medium without any selective antibiotics was used as negative control. SEAP secretion was detected by measuring the OD600 at 15 min, 1 h, 2 h, and 3 h after addition of 180 µL of QUANTI-Blue (Invivogen, CA, USA) to 20 µL of induced hTLR2 and hTLR4 supernatant. Experiments were performed in triplicate.

Results:

The results show that Amuc-1100 was able to interact with TLR2. Further, the results show that Amuc-1100 exerted immune-stimulatory effects on reporter cells expressing TLR2, i.e. Amuc-1100 was capable of stimulating the release of NF-κB from reporter cells.

Example 3. Stimulation of Cytokine Release from Peripheral Blood Mononuclear Cells Method:

The ability of Amuc-1100 to stimulate cytokine production or release from peripheral blood mononuclear cells (PBMCs) was tested in vitro. Briefly, peripheral blood of three healthy donors was received from the Sanquin Blood Bank, Nijmegen, The Netherlands. Peripheral blood mononuclear cells (PBMCs) were separated from the blood of healthy donors using Ficoll-Paque Plus gradient centrifugation according to the manufacturer's protocol (Amersham biosciences, Uppsala, Sweden). After centrifugation the mononuclear cells were collected, washed in Iscove's Modified Dulbecco's Medium (IMDM)+Glutamax (Invitrogen, Breda, The Netherlands) and adjusted to $0.5 \times 10^6$ cells/ml in IMDM+Glutamax supplemented with penicillin (100 U/ml) (Invitrogen), streptomycin (100 µg/ml) (Invitrogen), and 10% heat inactivated FBS (Lonza, Basel, Switzerland). PBMCs ($0.5 \times 10^6$ cells/well) were seeded in 48-well tissue culture plates. For each donor, a negative control (medium only) was used.

The PBMCs were stimulated with *A. muciniphila* cells (1:10 ratio to PBMCs) either alive or heated for 10 min at 99° C.) or Amuc-1100 for 1 day and subsequently the production of cytokine IL-6, IL-8, IL-10, TNF-α, IL-1β and IL-12p70 was measured in culture supernatants using multiple analysis (Human inflammation CBA kit, Becton and Dickinson) according to the manufacturer's protocol on a FACS Cantoll (Becton Dickinson) and analysed using BD FCAP software (Becton Dickinson). The detection limits according to the manufacturer were as follows: 3.6 pg/ml IL-8, 7.2 pg/ml IL-1β, 2.5 pg/ml IL-6, 3.3 pg/ml IL-10, 3.7 pg/ml TNF-α, 1.9 pg/ml IL-12p70.

Results

The results show that, compared to the control situation (medium only), Amuc-1100 was able to stimulate the production of cytokines, i.e. increased levels of IL-1β, IL-6, IL-8, IL-10 and TNF-α were observed. The level of cytokine induced by 4.5 µg/ml Amuc-1100 was at a similar level as that of $5 \times 10^6$ cells of *A. muciniphila* either alive or in a heat-killed form (see Table 1 below).

TABLE 1

Levels of cytokine induced by Amuc-1100 and *Akkermansia muciniphila* either alive or in a heat-killed form

| Cytokine (pg/ml) | Live *A. muciniphila* | Heat-killed *A. muciniphila* | Amuc-1100 (4.5 µg/ml) |
| --- | --- | --- | --- |
| IL-1β | 894 ± 298 | 392 ± 71 | 504 ± 227 |
| IL-6 | 18029 ± 309 | 13477 ± 2014 | 12508 ± 2362 |
| IL-8 | 60018 ± 18229 | 54230 ± 9030 | 45432 ± 12507 |
| IL-10 | 823 ± 310 | 638 ± 118 | 526 ± 180 |
| TNF-α | 1920 ± 349 | 957 ± 568 | 1317 ± 885 |
| IL-12p70 | <2 | <2 | <2 |

Example 4: Modulation of the Transepithelial Resistance (TER)

Method:

The ability of Amuc-1100 to promote the integrity of gut epithelial cell layer was assessed by measuring the ability of Amuc-1100 to stimulate or increase TER of Caco-2 cells in vitro. Briefly, Caco-2 cells ($5 \times 10^4$ cells/insert) were seeded in Millicell cell culture inserts (3 µm pore size; Millipore) and grown for 8 days. Bacterial cells were washed once with RPMI 1640, and applied onto the inserts at OD600 nm of 0.25 (approximately $10^8$ cells) in RPMI 1640. Purified Amuc-1100 was applied onto the inserts at concentrations of 0.05, 0.5 and 5 µg/ml. The transepithelial resistance was determined with a Millicell ERS-2 TER meter (Millipore) from cell cultures at time points 0 h, and 24 h after addition of Amuc-1100.

Results:

The results showed that already 0.05 µg/ml of Amuc-1100 was able to significantly increase TER after 24 h of co-cultivation with the Caco-2 cells at a similar level of approximately $10^8$ *A. muciniphila* cells.

Example 5: Modulation of Diet-Induced Metabolic Dysfunction

Figure 1:
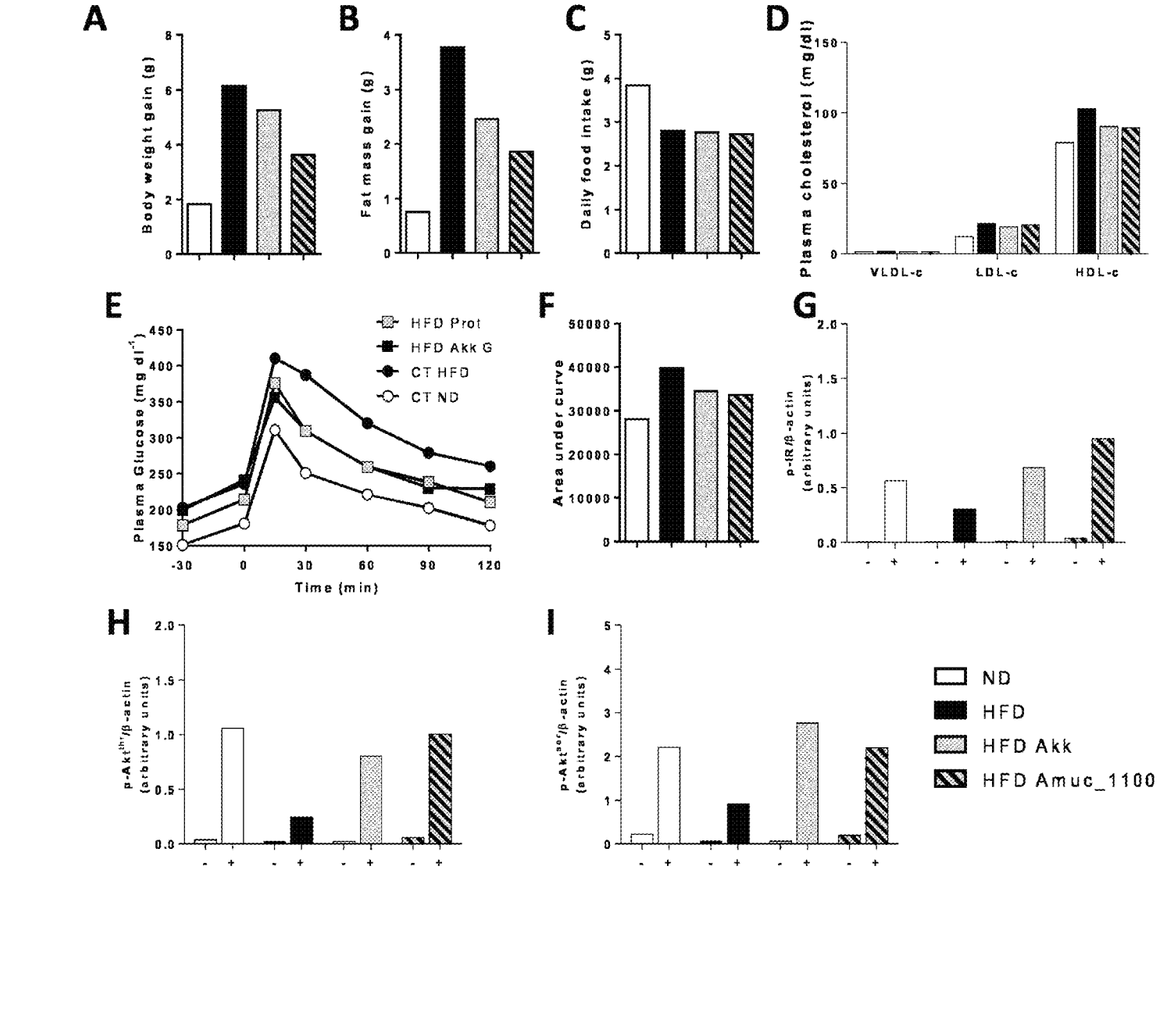
FIG. 1 shows: A) Total body weight gain (g) (n=8-10). B) Total fat mass gain (g) measured by Time domain-Nuclear magnetic resonance (n=8-10). C) daily food intake. D) Plasma VLDL, LDL and HDL cholesterol levels (n=8-10). E) Plasma glucose (mg dl$^{-1}$) profile and F) mean area under the curve (AUC) measured between −30 and 120 min after glucose loading (mg·dl$^{-1}$·min$^{-1}$; n=8-10). G) Ratio of the control and insulin-stimulated p-IRβ on the loading control as measured by densitometry (n=3-5). H and I) Ratio of the control and insulin-stimulated p-Akt$^{thr308}$ and p-Akt$^{ser473}$ on the loading control as measured by densitometry (n=3-5).

A cohort of 10-11 week-old C57BL/6J mice (n=10 per subset) was fed a control diet (ND) or an HF diet (HFD; 60% fat and 20% carbohydrates (kcal/100 g) D12492i, Research Diet, New Brunswick, N.J., USA) as previously described by Everard et al. (2013. PNAS. Vol. 110(22):9066-9071). *A. muciniphila* Muc$^T$ was grown on a synthetic medium (containing per liter deionized water: 0.4 g $KH_2PO_4$, 0.669 g $Na_2HPO_4.2H_2O$, 0.3 g $NH_4Cl$, 0.3 g NaCl, 0.1 g $MgCl_2.6H^2O$, 10 g Casitone, 1 mM L-threonine, 1 ml trace mineral solution, 5 mM L-fucose and 5 mM D-glucose) as described by Lucovac et al. (2014, mBio 01438-14) and concentrated, formulated in PBS containing 25% glycerol, and stored at −80° C. as described by Everard et al. supra. A subset of mice receiving HFD additionally received, daily and by oral gavage, $2 \times 10^8$ cfu/0.15 ml *A. muciniphila* suspended in sterile anaerobic PBS (HFD Akk)—since this included a 10-fold dilution of the *A. muciniphila*, a final concentration of 2.5% glycerol was obtained. The ND and HFD groups were treated daily with an oral gavage of an equivalent volume of sterile anaerobic PBS containing 2.5% glycerol, as previously described by Everard et al., supra. A further subset of mice receiving HFD additionally received Amuc-1100 peptide delivered by daily oral gavage of 3.1 µg of the protein Amuc_1100 in an equivalent volume of sterile PBS containing 2.5% glycerol. Treatment of HFD-fed mice with Amuc-1100 caused a similar or even more prominent decrease in body weight and fat mass gain when compared to the live *A. muciniphila* bacterium (FIGS. 1 A and B), without affecting food intake (FIG. 1 C). Treatment with *A. muciniphila* or Amuc-1100 also corrected the HFD-induced hypercholesterolemia, with a significant decrease in serum HDL-cholesterol and a similar trend for LDL-cholesterol (FIG. 1 D).

Remarkably, treatment with Amuc-1100 led to a significant decrease of serum triglycerides when compared to untreated HFD-fed mice. Moreover, Amuc-1100 treatment also reduced the adipocyte mean diameter from 38 micrometer in HFD-fed mice to 29 micrometer, a similar diameter as found in untreated mice (27 micrometer).

Interestingly, administration of Amuc-1100 reduced glucose intolerance with the same potency as the live bacterium (FIG. 1 E-F).

To further investigate glucose metabolism we investigated insulin sensitivity by injecting insulin in the portal vein. We analyzed insulin-induced phosphorylation of the insulin receptor (IR) and its downstream mediator Akt in the liver at the threonine ($Akt^{thr}$) and serine ($Akt^{ser}$) sites (FIG. 1 G). Administration of the HFD led to a decreased phosphorylation of all proteins when compared to mice fed a control chow, reaching significance in the case of $Akt^{thr}$ (FIG. 1 H). Treatment with live *A. muciniphila* or Amuc-1100 counteracted these effects, with significantly higher levels of p-IR and p-$Akt^{thr}$ in mice treated with Amuc-1100 (FIG. 1 G-H) and significantly higher levels of p-$Akt^{ser}$ in mice treated with the live bacterium (FIG. 1 I) when compared to the untreated HFD-fed mice.

The invention claimed is:

1. A method for treating a disease or disorder associated with an impaired gut barrier or immune cell function in a subject in need thereof, comprising
administering to the subject an effective amount of an isolated polypeptide having at least 90% identity to the amino acid sequence of SEQ ID NO:1 over the entire length of SEQ ID NO:1,
thereby treating the subject of the disease or disorder.

2. The method of claim 1, wherein the isolated polypeptide comprises the amino acid sequence set forth in SEQ ID NO:1.

3. The method of claim 1, wherein the disease or disorder is:

a metabolic condition selected from the group consisting of: obesity; metabolic syndrome; insulin-deficiency; insulin-resistance related disorders; type 2 diabetes; type 1 diabetes; gestational diabetes; glucose intolerance; abnormal lipid metabolism; hyperglycemia; dyslipidemias; obesity; high cholesterol; and elevated triglycerides;

an inflammatory or immune condition selected from the group consisting of: inflammatory bowel disease (IBD); irritable bowel syndrome (IBS); non-alcoholic fatty liver disease; alcoholic fatty liver disease; hepatic steatosis; gallbladder disease; allergy; asthma; osteoarthritis; and cancer;

a vascular or cardiovascular condition selected from the group consisting of: preeclampsia; atherosclerosis; cardiovascular disease; cardiac pathology; hypertension; stroke; and wound healing; or a behavioral or neurological condition selected from the group consisting of: autism; Parkinson's disease; multiple sclerosis; neurodegenerative disease; depression; alcohol dependence; and sleep apnea.

4. The method of claim 1, wherein the impaired gut barrier function is a result of one or more causes selected from the group consisting of: food allergies; premature birth; immaturity of the gut; radiation; chemotherapy; toxins, autoimmune disorders; malnutrition; and sepsis.

5. The method of claim 1, wherein administering an effective amount of the polypeptide maintains, restores, and/or increases the physical integrity of the mucosal gut barrier and/or improves the gut mucosal immune system function of the subject.

6. The method of claim 1, wherein administering an effective amount of a polypeptide improves glucose, cholesterol, and/or triglyceride homeostasis, and/or promotes weight loss in the subject.

7. The method of claim 1, wherein the polypeptide is administered orally, intravenously, topically, enterally, or parenterally.

8. The method of claim 1, wherein the polypeptide is isolated from an *Akkermansia* bacterial species.

9. The method of claim 1, wherein the polypeptide is isolated from *Akkermansia muciniphila*.

10. A method for treating a disease or disorder associated with impaired gut barrier or immune cell function in a subject in need thereof, comprising
administering to the subject a genetically modified isolated host cell comprising a nucleic acid molecule encoding an isolated polypeptide having at least 90% identity to the amino acid sequence of SEQ ID NO:1 over the entire length of SEQ ID NO:1,
thereby treating the subject of the disease or disorder.

11. The method of claim 10, wherein the isolated polypeptide comprises the amino acid sequence set forth in SEQ ID NO:1, or wherein the isolated polypeptide comprises the nucleic acid sequence set forth in SEQ ID NO:2.

12. The method of claim 10, wherein the disease or disorder is:
a metabolic condition selected from the group consisting of: obesity; metabolic syndrome; insulin-deficiency; insulin-resistance related disorders; type 2 diabetes; type 1 diabetes; gestational diabetes; glucose intolerance; abnormal lipid metabolism; hyperglycemia; dyslipidemias; obesity; high cholesterol; and elevated triglycerides;
an inflammatory or immune condition selected from the group consisting of: inflammatory bowel disease (IBD); irritable bowel syndrome (IBS); non-alcoholic fatty liver disease; alcoholic fatty liver disease; hepatic steatosis; gallbladder disease; allergy; asthma; osteoarthritis; and cancer;
a vascular or cardiovascular condition selected from the group consisting of: preeclampsia; atherosclerosis; cardiovascular disease; cardiac pathology; hypertension; stroke; and wound healing; or
a behavioral or neurological condition selected from the group consisting of: autism; Parkinson's disease; multiple sclerosis; neurodegenerative disease; depression; alcohol dependence; and sleep apnea.

13. The method of claim 10, wherein the impaired gut barrier function is a result of one or more causes selected from the group consisting of: food allergies; premature birth; immaturity of the gut; radiation; chemotherapy; toxins, autoimmune disorders; malnutrition; and sepsis.

14. The method of claim 10, wherein administering the genetically altered host cell maintains, restores, and/or increases the physical integrity of the mucosal gut barrier and/or improves the gut mucosal immune system function of the subject.

15. The method of claim 10, wherein administering the genetically altered host cell improves glucose, cholesterol, and/or triglyceride homeostasis, and/or promotes weight loss in the subject.

16. The method of claim 10, wherein the polypeptide is isolated from an *Akkermansia* bacterial species.

17. The method of claim 10, wherein the polypeptide is isolated from *Akkermansia muciniphila*.

18. A method for treating a disease or disorder associated with impaired gut barrier or immune cell function in a subject in need thereof, comprising
administering to the subject an effective amount of a pharmaceutical composition comprising an isolated polypeptide having at least 90% identity to the amino acid sequence of SEQ ID NO:1 over the entire length of SEQ ID NO:1,
thereby treating the subject of the disease or disorder.

19. The method of claim 18, wherein the isolated polypeptide comprises the amino acid sequence set forth in SEQ ID NO:1.

20. The method of claim 18, wherein the disease or disorder is:
a metabolic condition selected from the group consisting of: obesity; metabolic syndrome; insulin-deficiency; insulin-resistance related disorders; type 2 diabetes; type 1 diabetes; gestational diabetes; glucose intolerance; abnormal lipid metabolism; hyperglycemia; dyslipidemias; obesity; high cholesterol; and elevated triglycerides;
an inflammatory or immune condition selected from the group consisting of: inflammatory bowel disease (IBD); irritable bowel syndrome (IBS); non-alcoholic fatty liver disease; alcoholic fatty liver disease; hepatic steatosis; gallbladder disease; allergy; asthma; osteoarthritis; and cancer;
a vascular or cardiovascular condition selected from the group consisting of: preeclampsia; atherosclerosis; cardiovascular disease; cardiac pathology; hypertension; stroke; and wound healing; or
a behavioral or neurological condition selected from the group consisting of: autism; Parkinson's disease; multiple sclerosis; neurodegenerative disease; depression; alcohol dependence; and sleep apnea.

21. The method of claim 18, wherein the impaired gut barrier function is a result of one or more causes selected from the group consisting of: food allergies; premature birth; immaturity of the gut; radiation; chemotherapy; toxins, autoimmune disorders; malnutrition; and sepsis.

22. The method of claim 18, wherein administering an effective amount of the pharmaceutical composition maintains, restores, and/or increases the physical integrity of the mucosal gut barrier and/or improves the gut mucosal immune system function of the subject.

23. The method of claim 18, wherein administering an effective amount of the pharmaceutical composition improves glucose, cholesterol, and/or triglyceride homeostasis, and/or promotes weight loss in the subject.

24. The method of claim 18, wherein the pharmaceutical composition is administered orally, intravenously, topically, enterally, or parenterally.

25. The method of claim 18, wherein the polypeptide is isolated from an *Akkermansia* bacterial species.

26. The method of claim 18, wherein the polypeptide is isolated from *Akkermansia municiphila*.

* * * * *